United States Patent [19]

Saito et al.

[11] Patent Number: 5,762,915

[45] Date of Patent: Jun. 9, 1998

[54] PHOTOCHROMIC ULTRA-VIOLET RAY SHIELD POWDER, METHOD OF MANUFACTURING THE SAME, AND SKIN EXTERNAL PREPARATION USING THE SAME

[75] Inventors: Tsutomu Saito; Fukuji Suzuki; Kazuhisa Ohno; Osamu Sakurai, all of Yokohama, Japan

[73] Assignee: Shiseido Co., Ltd., Tokyo, Japan

[21] Appl. No.: 695,527

[22] Filed: Aug. 12, 1996

Related U.S. Application Data

[63] Continuation of Ser. No. 372,910, Jan. 17, 1995, abandoned, which is a continuation of Ser. No. 896,615, Jun. 10, 1992.

[30] Foreign Application Priority Data

Jun. 10, 1991 [JP] Japan ..................... 3-106511

[51] Int. Cl.$^6$ .................. A61K 7/42; C09C 1/36; C01G 23/047
[52] U.S. Cl. .................. 424/59; 106/436; 423/610; 424/60
[58] Field of Search .................. 424/59, 60; 423/610; 106/436

[56] References Cited

U.S. PATENT DOCUMENTS

| | | | |
|---|---|---|---|
| 3,658,539 | 4/1972 | Dantro | 423/610 |
| 3,709,984 | 1/1973 | Dantro | 423/610 |
| 3,749,764 | 7/1973 | Basque et al. | 423/610 |
| 4,505,886 | 3/1985 | Cody et al. | 423/610 |
| 5,147,629 | 9/1992 | Robb et al. | 423/610 |

FOREIGN PATENT DOCUMENTS

| | | |
|---|---|---|
| 0359606 | 5/1989 | European Pat. Off. |
| 0444798 | 2/1992 | European Pat. Off. |
| 4038258 | 11/1990 | Germany |
| A62067014 | 3/1987 | Japan |
| A4139109 | 5/1988 | Japan |
| 63132811 | 6/1988 | Japan |

Primary Examiner—Shelley A. Dodson
Attorney, Agent, or Firm—Townsend & Banta

[57] ABSTRACT

A photochromic ultra-violet ray shield material principally composed of titanium oxide particles, which have a specific surface area of 25 m2/g or above and also have $\Delta E=5 \leq A$ (discoloration degrees) and B (at restoration)$<\Delta E=3$, a method of manufacturing the same and a skin external preparation using the same. Both photochromic property and excellent ultra-violet ray shield effect are obtained.

1 Claim, 6 Drawing Sheets

PHOTOCHROMIC ULTRA-VIOLET RAY SHIELD POWDER, METHOD OF MANUFACTURING THE SAME, AND SKIN EXTERNAL PREPARATION USING THE SAME

This application is a file wrapper continuation of application Ser. No. 08/372,910, filed Jan. 17, 1995, which is a continuation of application Ser. No. 07/896,615 filed Jun. 10, 1992.

FIELD OF THE INVENTION

This invention relates to photochromic ultra-violet ray shield powder method of manufacturing the same and skin external preparation using the same and, more particularly to imparting ultra-violet ray shield powder, principally composed of titanium oxide, with the photochromic property.

BACKGROUND ART

The property of changing color when one substance is irradiated with light and then returning to its original color when the light irradiation is stopped, is referred to as the photochromic property or phototropic property. This property is utilized for color control glasses or the like containing photochromic materials.

In the field of cosmetics, color variable make-up preparation which utilize the photochromic property and permit enjoyment of color changes, is well known (as disclosed in Japanese Patent Application Laid-Open 49312/1981, Japanese Patent Application Laid-Open 10079/1981 and PCT WO 89/12084), and their applications in broader fields are expected.

Meanwhile, in the field of cosmetics there is problems of adverse effects of ultra-violet rays on the skin, and ultra-violet ray absorbers for absorbing ultra-violet rays and also ultra-violet ray shield powder for shielding ultra-violet rays have been developed.

A typical example of the ultra-violet ray shield powder is fine particle titanium oxide which can scatter ultra-violet rays, and also there is titanium oxide having photochromic property. Therefore, photochromic titanium oxide which has both of these properties has been thought of.

SUMMARY OF THE INVENTION

The present invention has been intended in the light of the above problems in the prior art, and its object is to provide a Photochromic ultra-violet ray shield powder, which has both ultra-violet ray shield effect and excellent photochromic property.

To attain the above object of the invention, the inventors have conducted extensive researches and investigations conditions for imparting Nine particle titanium oxide with the photochromic property and agglomeration properties. They found that powder having excellent photochromic property and ultra-violet ray shield effect could be obtained by manufacturing it under specific conditions in correspondence to the specific surface area of the material fine particle titanium oxide. The invention is completed on the basis of this finding.

According to claim 1 of the present application, there is provided a photochromic ultra-violet ray shield powder principally composed of particles with specific surface area of 25 $m^2/g$ or above and $A \geq 5$ and $B \leq 3$, A and B being determined as follows 4 g of the powder is uniformly dispersed in 16 g of nitrocellulose lacker to form a dispersion, which is coated on art paper using an applicator to form a coating film with thickness of 76 μm, which coating film is in turn dried to be used as a sample for photochromic property measurement under an optical condition that a lame ("FL20S.BLB" manufactured by Toshiba) and a lamp ("FL20S-E" manufactured by Toshiba) are secured at a distance of 11 cm from each other. Distance adjustment of the sample is effected using an ultra-violet ray intensity measuring apparatus ("SUV-T" manufactured by Tolay Technso) such that the intensity of ultra-violet rays incident on the sample is 2 $mW./cm^2$.

(1) The sample is colorimetrically measured after it has been left at room temperature and in a dark place for about 10 hours the measurement being made using a colorimeter ("CR-200" manufactured by Minolta).

(2) The sample is immediately colorimetrically measured when it is darkened by irradiation with the ultra-violet rays for 30 minutes in same way as described above.

(3) The irradiated sample is similarly colorimetrically measured after leaving it at room temperature and in a dark place for 24 hours.

A represent the color difference ΔE between the color determined in (1) and the color determined in (2).

B represents the color difference ΔE between the color determined in (1) and the color determined in (3).

According to claim 2, there is provided photochromic ultra-violet ray shield powder, which is principally composed of titanium oxide.

According to claim 3, there is provided photochromic ultra-violet ray shield powder, which contains at least 50% of anatase type titanium oxide.

According to claim 4, there is provided photochromic ultra-violet ray shield powder, which contains a photochromic property imparting agent metal Me such that $$0.05 \geq MeO_m/(MeO_m + TiO_2) \geq 0.0001$$

m=½, 1, 3/2, 2 or 3.

According to claim 5, there is provided a photochromic ultra-violet ray shield powder obtainable by calcinating material titanium oxide with a specific surface area of 100 $m^2/g$ or above at a temperature of 700° C. or below.

According to claim 6 there is provided a method of manufacturing photochromic ultra-violet ray shield powder, which comprises the step of calcinating material titanium oxide with a specific surface area of $S_0$ $m^2/g$ ($S_0$ being 100 or above) at a temperature of T° C. calculated by relations (1) below;

Relations (1):

$$T(S_0+10)^{0.10}$$

$$400 \leq T \leq 600$$

According to claim 7, there is provided a method of manufacturing photochromic ultra-violet ray shield powder, in which the photochromic property imparting agent metal being in the form of salt or alkoxide and precipitated by solution of the salt or the alkoxide by neutralization or hydrolysis reaction.

According to claim 8, there is provided a method of manufacturing photochromic ultra-violet ray shield powder, the pH is controlled to 8 to 11 during the neutralization.

According to claim 9, there is provided a skin external preparation containing 0.1 to 60% by weight of the photochromic ultra-violet ray shield powder.

Now, the constitutions of the invention will be described in detail.

Titanium oxide used as material according to the invention may be titanium dioxide lower titanium oxide, etc. These titanium oxide varieties may be used in combinations. Titanium dioxide may be of anatase type, rutile type and amorphous. Any of these varieties may be used. Suitably, at least 50% of anatase type titanium oxide may be contained because in this case satisfactory photochromic property can be obtained. The particles may be indefinite, flaky or spherical in shape The material titanium oxide used according to the invention may be those obtained by a gaseous phase process, a liquid phase process and various other processes.

The gaseous phase process is one, in which halotitanium in the form of vapor or gas is decomposed at a high temperature together with an oxidizing agent or a hydrolysis agent to obtain titanium oxide.

The liquid phase process is one, in which titanium tetra-iso-propoxide or the like subjected to hydrolysis to obtain titanium oxide.

The size of the titanium oxide particles after calcinating is suitably 25 $m^2/g$ or above, preferably 40 to 100 $m^2/g$, in terms of the specific surface area. If the size is less than 25 $m^2/g$ or greater than 100 $m^2/g$, the ultra-violet ray shield effect tends to be reduced.

The proportion of titanium oxide used in the manufacture of photochromic fine particle titanium oxide, is suitably 95.0 to 99.99% by weight.

Examples of the metal used to impart titanium oxide with the photochromic property, are iron, zinc, aluminum, silicon, etc. These metals may be used in the form of their powder or as their salts, e.g. sulfates, chlorides, nitrates and acetates, or oxides, hydrates, hydroxides, etc. The photochromic property may also be imparted using cobalt, cerium, etc. In this case, however, the powder itself is colored, undesirably making it difficult in actual practice to observe the photochromic property.

Particularly, metallic iron powder and iron compounds are suitable from the standpoints of the safety in human use and imparting with the photochromic property. According to the invention, metallic iron powder and iron compounds may be used alone or in their suitable combinations. Examples of the iron compound are salts of iron, e.g. iron sulfate, iron chloride, iron nitrate, iron acetate, etc., and also iron oxide and iron hydroxide.

The proportion of the metal used to impart with the photochromic property in the manufacture of photochromic titanium oxide, is suitably 0.1 to 5.0% by weight, preferably 0.5 to 1.5 by weight. If the proportion of the metal is insufficient, it is liable to result in insufficient photochromic property. If the proportion is excessive, on the other hand, undesired coloring is liable.

Further, according to the invention it is possible to compound the photochromic ultra-violet ray shield powder with other inorganic or organic compounds For example, the photochromic fine particle titanium oxide may be mixed with or compounded by means of coating or calcinating with one or more members of the group consisting of inorganic compounds, e,g., mica, sericite, talc, kaolin, silica, barium sulfate, iron oxide, chromium oxide, copper oxide, nickel oxide, vanadium oxide, manganese oxide, cobalt oxide, calcium oxide, magnesium oxide, molybdenum oxide, zinc oxide, iron, chromium, copper, nickel, vanadium, manganese, etc., and organic compounds, e.g., nylon, polymethyl methacrylate, polystyrene, epoxy resins, polyethylene, etc.

Further, ordinary titanium oxide may be compounded with other inorganic or organic compounds to impart with the photochromic property.

A composite material containing photochromic titanium oxide may be obtained by adding 0.1 to 0.5% by weight of metallic iron particles or iron compounds to a composite material such as titanium-mica or titanium-talc coated with titanium dioxide by a dry process using a ball mill or the like or by a wet process of adding the system in the form of an aqueous solution and then calcinating the resultant system. In an alternative method, a titanium dioxide composite material by means of the hydrolysis of titanyl sulfate in the presence of metallic iron powder or iron compounds and then calcinated.

According to the invention, the composite material containing photochromic titanium oxide may be used after subjecting it to surface treatment, e.g., silicone treatment, surfactant treatment, surface alkoxyl treatment, metallic soap treatment, fatty avid treatment, fluorine resin treatment, wax treatment, etc. By improving temp dispersion property in this way, it is possible to further improve the ultra-violet ray shield performance and photochromic property.

When using the photochromic ultra-violet ray shield powder for a shin external preparation, its proportion in the total composition is suitably 1.0 to 60.0% by weight, preferably 5.0 to 20.0% by weight. If the proportion is less than 1% by weight, the color change function may not be provided. If the proportion is over 30% by weight, on the other hand, the color change degree may often be excessive.

When flaky titanium oxide is used to manufacture the photochromic ultra-violet ray shield powder, the proportion in the total composition is suitably 10 to 60% by weight, preferably 10 to 40% by weight. The reason for increasing the proportion compared to the case of using the fine particle titanium oxide as the material, is that the color change degree per unit weight is reduced with increased particle size of the flaky titanium oxide.

Likewise, when incorporating the fine particle photochromic ultra-violet ray shield powder is incorporated in a foundation or a powdery make-up preparation such as loose powder or pressed powder, it is suitably incorporated in 1 to 30% by weight. If its content is less than 1% by weight, sufficient photochromic property cannot be obtained. If the content is over 30% by weight, on the other hand, excessive color tore change is liable.

When using flaky titanium oxide as titanium oxide, it is suitably incorporated by 10 to 60% ban weight with respect to powdery cosmetics.

When the fine particle photochromic titanium oxide in liquid cosmetics such as sun oil, it is suitably incorporated in 1 to 30% by weight.

If the proportion exceeds 30% by weight, the viscosity will excessively increased, and in this case it is difficult to provide the function of the liquid cosmetics.

The composition incorporating the photochromic ultra-violet ray shield powder according to the invention, may suitably incorporate, if desired, other components usually used for the compositions of cosmetics or the like. For example, it may incorporate inorganic powder, e.g., talc, kaolin, mica, sericite, white mica, gold mica, synthetic mica, red mica, black mica, rithia mica, vermicurite, magnesium carbonate calcium carbonate, diatomaceocus earth, magnesium silicate, calcium silicate, aluminum silicate, barium silicate, barium sulfate, strontium, silicate, tungstate metal salts, silica, magnesium oxide, calcium oxide, zeolite, boron nitride, ceramic powder, etc., organic powder, e.g., nylon powder polyethylene powder, benzoguanamine powder, tetrafluoroethlyene powder, fine crystalline cellulose, etc., inorganic white pigments, e.g., titanium dioxide, zinc oxide, etc., inorganic red pigments, e.g., iron oxide (red iron oxide), iron titanate, etc., inorganic brawl pigments, e.g., γ-iron oxide, etc., inorganic yellow pigments, e.g., yellow iron oxide, less, etc., inorganic black pigments, e.g., black iron oxide, carbon black, etc., inorganic violet pigments, e.g., mango violet cobalt violet, etc., inorganic green pigments, e.g., chromium oxide, chromium hydroxide, cobalt titanate, etc., inorganic blue pigments, e.g., ultramarine, red marine, etc., pearl pigments, e.g., mica coated with titanium dioxide, bismuth oxychloride coated with titanium dioxide, bismuth oxychloride, talc coated with titanium oxide, mica coated with colored titanium oxide, etc., metal powder pigments, e.g., aluminum powder, copper powder, etc., such organic pigments as "Red No. 201", "Red No.. 202", "Red NO. 204", "Red No. 205", "Red No. 220", "Red No. 226", "Red No. 228", "Red No. 405", "Orange No. 203", "Orange No. 204", "Yellow No. 205", "Yellow No. 401", "Blue No. 404", etc. and such organic pigments as "Red No. 3", "Red No. 104", "Red No. 106", "Red No. 227", "Red No. 230", "Red No. 401", "Red No. 505", "Orange No. 205", "Yellow No. 5", "Yellow No. 202", "Yellow No. 203", "Green No. 3", "Blue No. 1", zirconium, barium, aluminum lake, etc., natural dyestuffs, e.g., chlorophyll, β-kalotin, etc., various hydrocarbons e.g., squalane, liquid paraffin, vaseline, microcrystalline wax, ozokelite, serecile, cetylalcohol, hexadecylalcohol, oleilalcohol, cetyl-2-ethyl hexanoate, 2-ethylhexyl permiate, 2-octyldodecyl myristate, 2-octyldodecylgum ester neopentylglycol-2-ethyl hexanoate triglyceril iso-octanoate 2-ocylidodecyl oleate, iso-propyl myristate, triglyceril iso-stearate, coconut oil fatty acid triglyceride, olive oil, avocade oil, bees way, myristyl myristate, mink oil, ranoline, dimethylpolysiloxane, etc., oil, e.g., fat and oil, esters, higher alcohols, solders, silicone oil, etc., ultra-violet ray absorbers, anti-oxidization agents, surface active agents, moisture retainers, perfumes, water, alcohol and viscosity increasing agents.

When the photochromic ultra-violet ray shield power according to the invention is used for a cosmetics, the cosmetics may be powdery, cake-like, pencil-like, stick-like, paste-like, liquid-like, emulsion-like, cream-like, etc.

With the use of the photochromic flaky titanium oxide, molding surface may be removed with puff with difficulty of caking. In addition, the slip can be improved when the cosmetics is applied to the skin, thus improving the property of use of the make-up preparation.

As shown, according to the invention by incorporating the photochromic ultra-violet ray shield powder in compositions, typically cosmetics, it is possible to obtain photochromic property, which could not have been attained with the prior art materials of cosmetics products. Besides, because of high ultra-violet ray shield effect, It is possible to eliminate adverse effects of excessive ultra-violet rays on the skin. Further, the composition is highly stable with respect to light, and it does not cause any fatigue phenomenons. Thus, it is possible to obtain stable products.

Further, photochromic titanium oxide is far more stable than photochromic organic materials.

The photochromic ultra-violet ray shield powder may be used for paints as well as for cosmetics.

BEST MODE FOR CARRYING OUT THE INVENTION

Now preferred mode of carrying out the invention will be described with reference to the drawings, without any sense of limiting the invention. Proportions are shown in % by weight if they are not particularly specified.

Definition of the photochromic property

According to the invention, the photochromic property is tested as follows.

4 g of photochromic ultra-violet ray shield powder is uniformly dispersed in 16 g of nitrocellulose lacker to form a dispersion. The dispersion is coated on art paper using an applicator to form a coating film with thickness of 76 μm. The coating film is then dried and used as a sample for photochromic property measurement under an optical condition that a lamp ("FL20.BLB " manufactured by Toshiba) and a lamp ("FL20S.E" manufactured by Toshiba) are secured at a distance of 11 cm from each other. Distance adjustment of the sample is effected using an ultra-violet ray intensity measuring apparatus ("SUV-T" manufactured by Tolay Techno) such that the intensity of ultra-violet rays incident on the same is 2 mW/cm$^2$.

Actual colorimetric measurements are done as follows (1) The sample is colorimetrically measured after it has been left at room temperature and in a dark place for about 10 hours, the measurement being made using a colorimeter ("CR-200" manufactured by Minolta).

(2) The sample is immediately colorimetrically measured when it is darkened by irradiation with the ultra-violet rays for 30 minutes in same way described above.

(3) The irradiated sample is similarly colorimetrically measure after leaving it at room temperature and in a dark place for 24 hours. The photochromic property is defined as $5 \leq A$, and $B \leq 3$, where A represents the color difference ΔE between the color determined in (1) and the color determined in (2), and B represents the color difference ΔE between the color determined in (1) and the color determined in (3).

Relation between specific surface area and calcinating temperature

In order to study for the cause of reduction of the ultra-violet ray shield effect of titanium oxide powder having ultra-violet ray shield effect as a result of imparting the powder with the photochromic property the inventors examined the relation between the specific surface area and calcinating temperature.

The titanium oxide having specific surface area of 98 m$^2$/g was calcinated at 600° to 1.000° C., and the specific surface area after the calcinating was measured.

Figure 1:
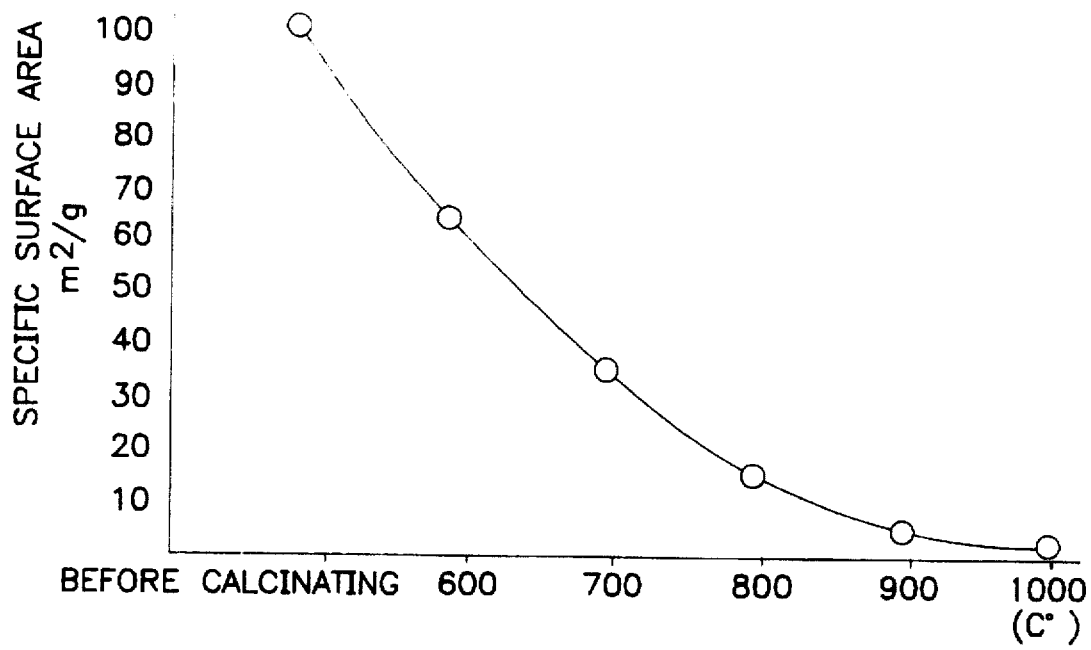
FIG. 1 is a graph showing the relation between the specific surface area and calcinating temperature of titanium oxide.

Results as shown in Table 1 and FIG. 1 were obtained.

TABLE 1

| Calcinating temperature | Specific surface area (m²/g) |
|---|---|
| Before calcinating | 98 |
| 600 | 66.3 |
| 700 | 36.9 |
| 800 | 15.5 |
| 900 | 6.0 |
| 1,000 | 3.5 |

It will be understood frog Table 1 above that with the increase the calcinating temperature the specific surface area is reduced, while the particle size is increased.

In this way, with reduction of the specific surface area i.e., with increase of the particle size, the ultra-violet ray shield effect of fine particle titanium oxide powder is reduced.

Meanwhile, in the prior art for imparting titanium oxide with the photochromic property, calcinating at about 600° C. or above is usually required, and photochromic ultra-violet ray shield powder laving satisfactory photochromic property and satisfactory ultra-violet ray shield effects has not been obtained.

The inventors, accordingly, conducted further investigations about the photochromic property of fine particle titanium oxide.

Relation between the photochromic property and manufacture method thereof

The photochromic property is influenced by the method of manufacture

Typical processes of imparting titanium oxide with the photochromic property are a neutralization process and an urea process.

Neutralization process

Figure 2:
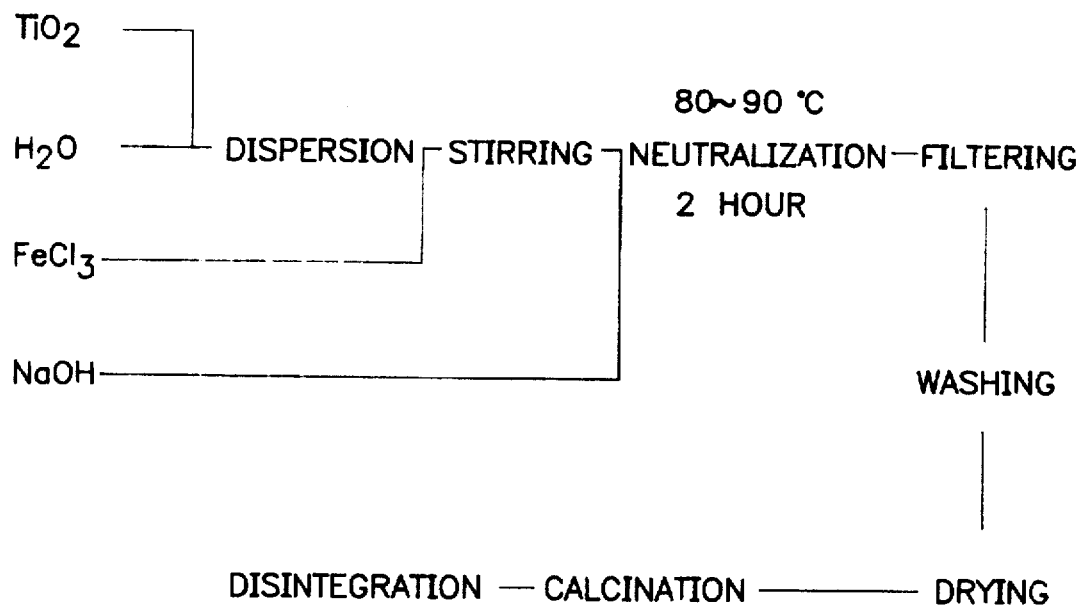
FIG. 2 is a view illustrating a process of manufacture of photochroinic titanium oxide by a neutralization process.

In the neutralization process, as shown in FIG. 2, titanium oxide is dispersed in deionized water, and he dispersion is stirred with iron chloride $FeCl_3$ added to it. The system is then neutralized by adding sodium hydroxide, and reacted at 80° to 90° C. for 2 hours. The reacted system is then filtered, and the residue is washed with water, then dried, then calcinated and then disintegrated.

Photochromic property is shown as color difference ΔE in case of using rutile type titanium oxide as titanium oxide in Table 2, and in case of using anatase type titanium oxide in Table 3.

The restoration factor is given as:

(ΔE after ultra-violet ray irradiation-ΔE after leaving in dark place)/(ΔE after ultra-violet ray irradiation)

The symbols shown under the numerical values of ΔE after ultra-violet ray irradiation for 30 minutes and ΔE after leaving in dark place for 24 hours concern judgment as to whether the values meets the definition noted above of the photochromic property (○: meets △: substantially meets, X: fails to meet)

TABLE 2

| Neutralization process (rutile type, specific surface area: 98 m²/g, 0,7% $Fe_2O_3$) | | | | | |
|---|---|---|---|---|---|
| Calcinating temperature | 600 | 660 | 700 | 800 | 900 |
| ΔE after ultra-violet ray irradiation for 30 minutes | 3.44 | 3.37 | 2.96 | 2.63 | 2.81 |

TABLE 2-continued

| Neutralization process (rutile type, specific surface area: 98 m²/g, 0,7% $Fe_2O_3$) | | | | | |
|---|---|---|---|---|---|
| (A) | X | X | X | X | X |
| ΔE after leaving in dark place for 60 minutes | 2.13 | 2.03 | 1.63 | 1.88 | 1.00 |
| Restoration factor | 38% | 40% | 45% | 29% | 65% |
| ΔE after leaving in dark place for 24 hours | 0.98 | 0.88 | 0.93 | 1.04 | 0.51 |
| (B) | ○ | ○ | ○ | ○ | ○ |
| Restoration factor | 78% | 74% | 69% | 61% | 82% |

TABLE 3

| Neutralization process (anatase type, 98 m²/g, 0.7% $Fe_2O_3$) | | | | | |
|---|---|---|---|---|---|
| Calcinating temperature | 600 | 660 | 700 | 800 | 900 |
| ΔE after ultra-violet ray irradiation for 30 minutes | 6.61 | 8.16 | 8.83 | 7.00 | 5.75 |
| (A) | ○ | ○ | ○ | ○ | ○ |
| ΔE after leaving in dark place for 60 minutes | 3.65 | 5.76 | 6.66 | 5.95 | 2.34 |
| Restoration factor | 45% | 30% | 25% | 15% | 60% |
| ΔE after leaving in dark place for 120 minutes | 3.07 | 5.02 | 6.09 | 5.52 | 2.17 |
| Restoration factor | 54% | 39% | 32% | 22% | 63% |
| ΔE after leaving in dark place for 24 hours | 1.88 | 3.15 | 3.96 | 4.02 | 1.45 |
| Restoration factor | 72% | 62% | 56% | 43% | 75% |

When the material titanium oxide used under the above conditions is rutile type, the color change degree is small, and substantially sufficient photochromic property can not be obtained.

When the anatase type is used, the photochromic property can be extremely improved compared to the case of using the rutile type. Also the color chance degree is large, i.e. 660° to 700° C. However it is suitably about 600° C. when the restoration factor is also taken into considerations.

Concerning the neutralization process, it is thought that the photochromic property is influenced by the pH at the time of the neutralization.

Accordingly, the inventors conducted researches of the photochromic property with different pH settings in the neutralization process. Tables 4 to 6 show the results.

TABLE 4

| Neutralization process pH: 8 (anatase type, specific surface area: 98 m²/g, 0.7% $Fe_2O_3$) | | | | |
|---|---|---|---|---|
| Calcinating temperature | 600 | 660 | 700 | 800 |
| ΔE after ultra-violet irradiation for 30 minutes | 8.03 | 10.00 | 11.00 | 9.46 |
| (A) | ○ | ○ | ○ | ○ |
| ΔE after leaving in dark place for 60 minutes | 4.73 | 7.57 | 8.99 | 7.90 |
| Restoration factor | 42% | 25% | 19% | 17% |
| ΔE after leaving in dark place for 24 hours | 2.68 | 5.01 | 6.34 | 5.57 |
| (B) | ○ | X | X | X |
| Restoration factor | 67% | 50% | 43% | 33% |

TABLE 5

Neutralization process
pH: 9 (anatase type, specific surface area: 98 m²/g, 0.7% Fe₂O₃)

| Calcinating temperature | 600 | 660 | 700 | 800 |
|---|---|---|---|---|
| ΔE after ultra-violet ray irradiation for 30 minutes | 6.31 | 7.61 | 9.59 | 4.59 |
| (A) | ○ | ○ | ○ | Δ |
| ΔE after leaving in dark place for 60 minutes | 3.07 | 5.06 | 5.54 | 3.51 |
| Restoration factor | 52% | 34% | 48% | 24% |
| ΔE after leaving in dark place for 24 hours | 1.71 | 3.08 | 3.66 | 2.42 |
| (B) | ○ | Δ | Δ | ○ |
| Restoration factor | 73% | 60% | 62% | 48% |

TABLE 6

Neutralization process
pH: 10 (anatase type, 98 m²/g, 0.7% Fe₂O₃)

| Calcinating temperature | 600 | 660 | 700 | 800 |
|---|---|---|---|---|
| ΔE after ultra-violet irradiation for 30 minutes | 6.17 | 7.05 | 8.09 | 5.28 |
| (A) | ○ | ○ | ○ | ○ |
| ΔE after leaving in dark place for 60 minutes | 2.70 | 4.24 | 5.73 | 4.26 |
| Restoration factor | 57% | 40% | 30% | 20% |
| ΔE after leaving in dark place for 24 hours | 1.25 | 2.30 | 3.48 | 2.78 |
| (B) | ○ | ○ | Δ | ○ |
| Restoration factor | 80% | 68% | 57% | 48% |

As is clear from Tables 4 to 6, by using anatase type titanium oxide, satisfactory color charge degree can be obtained with any of the pH 8 to 10. Considering the restoration factor, however, lower calcinating temperature is rather satisfactory. The color change degree is most satisfactory with pH 8. On the other hand, the restoration factor is the better the higher pH.

The relation between the photochroinic factor and pH was studied similarly in the case of using titanium oxide with anatase/rutile=75/25 as material.

Rutile type titanium oxide has a large refractive index and said to have greater ultra-violet ray shield effect than anatase type titanium oxide provided the particle size is the same. Therefore, when the ultra-violet ray shield effect is considered, it is suitable to incorporate rutile type titanium oxide.

Accordingly, researches were conducted on the Influence of incorporating rutile type titanium oxide in anatase type titanium oxide or the photochromic property.

Results are shown in Tables 7 to 9.

TABLE 7

Neutralization process
pH: 8 (anatase/rutile = 75/25 48 m²/g, 0.7% Fe₂O₃)

| Calcinating temperature | 600 | 660 | 700 | 800 |
|---|---|---|---|---|
| ΔE after ultra-violet ray irradiation for 30 minutes | 5.13 | 5.07 | 3.86 | 1.76 |
| (A) | ○ | ○ | X | X |
| ΔE after leaving in dark place for 60 minutes | 3.03 | 3.14 | 2.52 | 1.32 |
| Restoration factor | 41% | 39% | 35% | 25% |
| ΔE after leaving in dark place for 20 minutes | 2.78 | 2.67 | 2.23 | 1.22 |
| Restoration factor | 46% | 48% | 42% | 31% |
| ΔE after leaving in dark place for 24 hours | 1.08 | 0.73 | 0.36 | 0.52 |

TABLE 7-continued

Neutralization process
pH: 8 (anatase/rutile = 75/25 48 m²/g, 0.7% Fe₂O₃)

| (B) | ○ | ○ | ○ | ○ |
|---|---|---|---|---|
| Restoration factor | 79% | 86% | 91% | 70% |

TABLE 8

Neutralization process
pH: 9 (anatase/rutile = 75/25 48 m²/g, 0.7% Fe₂O₃)

| Calcinating temperature | 600 | 660 | 700 | 800 |
|---|---|---|---|---|
| ΔE after ultra-violet ray irradiation for 30 minutes | 4.92 | 4.30 | 4.57 | 1.26 |
| (A) | Δ | Δ | Δ | X |
| ΔE after leaving in dark place for 60 minutes | 2.99 | 2.30 | 2.99 | 0.80 |
| Restoration factor | 40% | 47% | 35% | 37% |
| ΔE after leaving in dark place for 120 minutes | 2.55 | 1.95 | 2.60 | 0.68 |
| Restoration factor | 48% | 55% | 43% | 46% |
| ΔE after leaving in dark place for 24 hours | 1.01 | 0.48 | 1.01 | 0.11 |
| (B) | ○ | ○ | ○ | ○ |
| Restoration factor | 80% | 89% | 78% | 91% |

TABLE 9

Neutralization process
pH: 10 (anatase/rutile = 75/25 48 m²/g, 0.7% Fe₂O₃)

| Calcinating temperature | 600 | 660 | 700 | 800 |
|---|---|---|---|---|
| ΔE after ultra-violet ray irradiation for 30 minutes | 4.89 | 4.42 | 5.16 | 1.36 |
| (A) | Δ | Δ | ○ | X |
| ΔE after leaving in dark place for 60 minutes | 2.59 | 2.42 | 3.32 | 0.76 |
| Restoration factor | 48% | 45% | 36% | 44% |
| ΔE after leaving in dark place for 120 minutes | 2.16 | 1.94 | 2.99 | 0.67 |
| Restoration factor | 56% | 56% | 42% | 51% |
| ΔE after leaving in dark place for 24 hours | 0.94 | 0.70 | 1.16 | 0.16 |
| (B) | ○ | ○ | ○ | ○ |
| Restoration factor | 81% | 84% | 78% | 88% |

As is clear from Tables 7 to 9, the rutile type incorporated reduces the color change degree but provides for satisfactory restoration factor. It is also to be understood that both the color change degree and restoration degree are satisfactory in the neighborhood of pH 8.

In the overall consideration of the above, it will be understood that when using the neutralization process it is suitable to use 75% or more of anatase type titanium oxide and effect a treatment about pH 8.

Urea process

The urea process is usually said be based on mild conditions of reaction, and it is possibly effective for prevention of the aggregation of titanium oxide.

Figure 3:
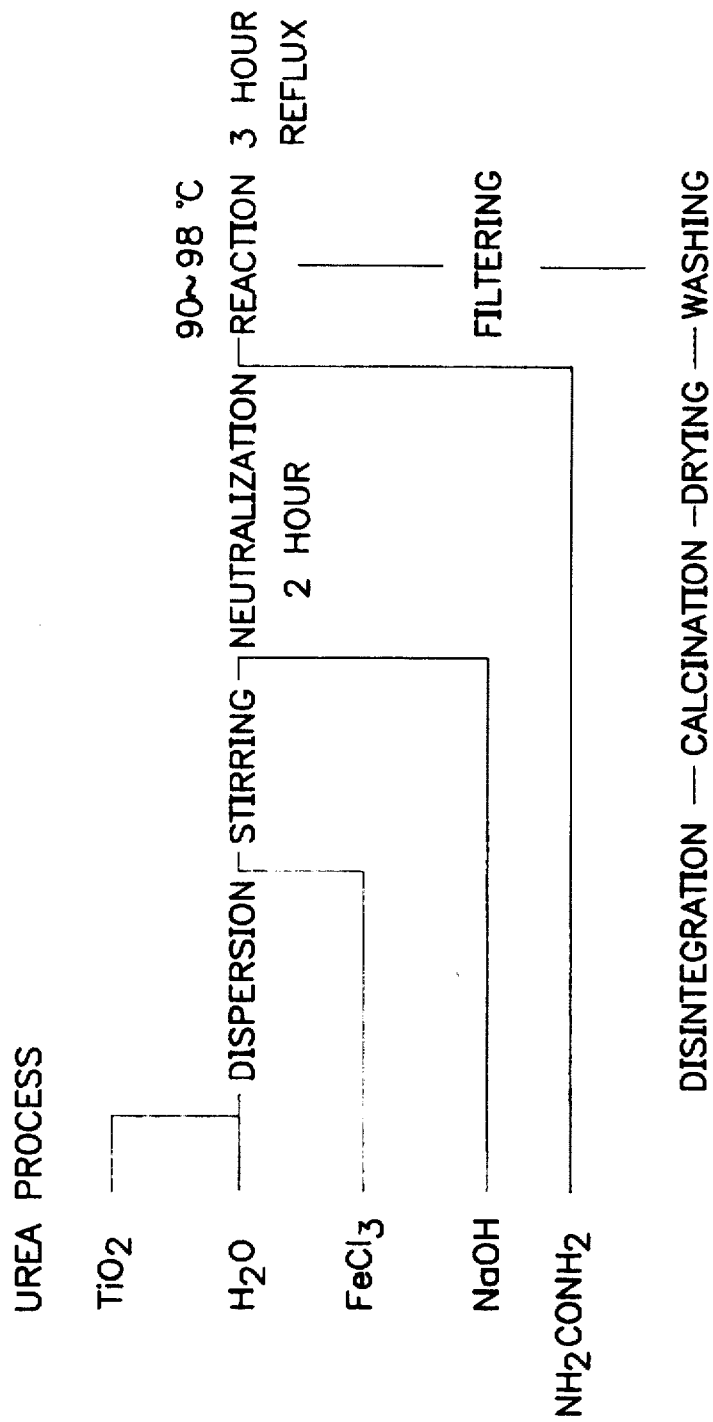
FIG. 3 is a view illustrating a process of manufacture of photochromic titanium oxide by a urea process.

In the urea process, as shown in. FIG. 3, titanium oxide is dispersed in deionized water and the system is stirred together with added iron chloride FeCl₃. Then, 5% sodium hydroxide aqueous solution was added for neutralization. Then, urea Is added, and to resultant system is reacted at 90° to 98° C. for 3 hours. Then, the reacted system is filtered, and the residue is washed with water, then dried, then calcinated and then disintegrated.

Tables 10 and 11 below show the photochromic property in terms of the color difference ΔE, respectively when rutile type titanium oxide is used as titanium oxide and when anatase type titanium oxide is used.

TABLE 10

Urea process
(rutile type, specific surface area: 98 m²/g, 0.5% Fe₂O₃)

| Calcinating temperature | 600 | 660 | 700 | 800 | 900 |
|---|---|---|---|---|---|
| ΔE after ultra-violet ray irradiation for 30 minutes (A) | 2.84 X | 2.92 X | 2.66 X | 2.19 X | 2.91 X |
| ΔE after leaving in dark place for 60 minutes | 1.39 | 1.77 | 1.35 | 1.35 | 0.77 |
| Restoration factor | 52% | 40% | 50% | 39% | 74% |
| ΔE after leaving in dark place for 24 hours | 0.98 | 0.80 | 0.57 | 0.60 | 0.45 |
| Restoration factor | 66% | 73% | 79% | 73% | 85% |

With rutile type titanium oxide used as material, the color change degree is small, and sufficient photochromic property can not be provided. The color change degree and restoration factor are thought to be independent of the calcinating temperature.

TABLE 11

Urea process
(anatase type 98 m²/g, 0.5% Fe₂O₃)

| Calcinating temperature | 600 | 660 | 700 | 800 | 900 |
|---|---|---|---|---|---|
| ΔE after ultra-violet irradiation for 30 minutes (A) | 7.83 ○ | 7.89 ○ | 7.74 ○ | 6.58 ○ | 2.54 X |
| ΔE after leaving in dark place for 60 minutes | 3.26 | 4.19 | 5.18 | 5.54 | 1.16 |
| Restoration factor | 59% | 47% | 34% | 16% | 54% |
| ΔE after leaving in dark place for 120 minutes | 2.49 | 3.61 | 5.01 | 5.23 | 1.04 |
| Restoration factor | 69% | 55% | 36% | 21% | 59% |
| ΔE after leaving in dark place for 24 hours (B) | 1.69 ○ | 2.14 ○ | 3.24 △ | 3.95 △ | 0.69 ○ |
| Restoration factor | 79% | 73% | 59% | 40% | 73% |

With anatase type titanium oxide used as the material, the lower the calcinating temperature the greater the color change degree as is seen from Table 11. In addition the restoration factor is the better the lower the calcinating temperature.

Further, in comparison to Table 3, the color change degree is great and also the restoration factor is satisfactory in a low calcinating temperature range.

It will be understood from the above that calcinating at a temperature lower than the common sense calcinating temperature in the prior art is effective for imparting fine particle titanium oxide with the photochromic property.

The fact that it Is possible to obtain satisfactory photochromic property at a low temperature, is very useful in view of the prevention of the aggregation during calcinating.

Accordingly the inventors conducted further researches concerning the photochromic property in a low calcinating temperature range.

Low temperature range calcinating and photochromic property

The inventors conducted researches concerning the relation between the low temperature calcinating and photochromic property.

TABLE 12

Neutralization process
pH: 8 (anatase type, specific surface area: 98 m²/g, Fe₂O₃ 0.7%)

| Calcinating temperature | 560 | 580 |
|---|---|---|
| ΔE after ultra-violet ray irradiation for 30 minutes (A) | 7.16 ○ | 7.38 ○ |
| {E after leaving dark place for 60 minutes | 3.47 | 4.18 |
| Restoration factor | 52% | 44% |
| ΔE after leaving in dark place for 120 minutes | 2.80 | 3.59 |
| Restoration factor | 61% | 52% |
| ΔE after leaving in dark place for 24 hours (B) | 1.58 ○ | 2.21 ○ |
| Restoration factor | 78% | 71% |

TABLE 13

Neutralization process
pH: 9 (anatase type, specific surface area: 98 m²/g, Fe₂O₃: 0.7%)

| Calcinating temperature | 560 | 580 |
|---|---|---|
| ΔE after ultra-violet ray irradiation for 30 minutes (A) | 6.13 ○ | 5.80 ○ |
| ΔE after leaving in dark place for 60 minutes | 2.26 | 2.46 |
| Restoration factor | 64% | 57% |
| ΔE after leaving in dark place for 120 minutes | 1.75 | 2.05 |
| Restoration factor | 72% | 65% |
| ΔE after leaving in dark place for 24 hours (B) | 0.93 ○ | 1.18 ○ |
| Restoring factor | 85% | 80% |

TABLE 14

Neutralization process
pH: 10 (anatase type, specific surface area: 98 m²/g, Fe₂O₃: 0.7%)

| Calcinating temperature | 560 | 580 |
|---|---|---|
| ΔE after ultra-violet ray irradiation for 30 minutes (A) | 6.26 ○ | 7.02 ○ |
| ΔE after leaving in dark place for 60 minutes | 2.10 | 3.26 |
| Restoration factor | 67% | 54% |
| ΔE after leaving in dark place for 120 minutes | 1.35 | 2.75 |
| Restoration factor | 79% | 61% |
| ΔE after leaving in dark place for 24 hours (B) | 0.60 ○ | 1.76 ○ |
| Restoration factor | 90% | 75% |

It will be understood from the above that by using the neutralization process with anatase, type titanium oxide as material, sufficient photochroinic property can be obtained at 560° to 580° C., which is lower than the temperature of 600° C. thought to be necessary for imparting with the photochromic property in prior art.

Further researches were conducted in case of incorporating rutile type titanium oxide.

TABLE 15

Neutralization process
(anatase/rutile = 75/25, specific surface area: 48 m²/g, Fe₂O₃: 1.0%)

| Calcinating temperature | 560 | 600 | 660 | 700 |
|---|---|---|---|---|
| ΔE after ultra-violet ray irradiation for 30 minutes | 5.29 | 5.62 | 5.38 | 5.02 |
| (A) | ○ | ○ | ○ | ○ |
| ΔE after leaving in dark place for 60 minutes | 3.52 | 3.34 | 3.64 | 3.32 |
| Restoration factor | 33% | 41% | 32% | 34% |
| ΔE after leaving in dark place for 120 minutes | 2.56 | 2.91 | 3.06 | 2.89 |
| Restoration factor | 52% | 48% | 43% | 42% |
| ΔE after leaving in dark place for 24 hours | 1.30 | 1.26 | 1.44 | 1.44 |
| (B) | ○ | ○ | ○ | ○ |
| Restoration factor | 75% | 78% | 73% | 71% |

TABLE 16

Neutralization process
(anatase/rutile = 75/25, specific surface area: 48 m²/g, Fe₂O₃: 2.0%)

| Calcinating temperature | 560 | 600 | 660 | 700 |
|---|---|---|---|---|
| ΔE after ultra-violet ray irradiation for 30 minutes | 3.72 | 3.87 | 3.53 | 3.15 |
| (A) | X | X | X | X |
| ΔE after leaving in dark place for 60 minutes | 2.41 | 2.45 | 2.43 | 1.93 |
| 120 minutes | 1.85 | 2.11 | 2.16 | 1.70 |
| 24 hours | 0.97 | 1.18 | 1.20 | 0.94 |

As is seen from Tables 15 and 16, where rutile type titanium oxide is incorporated by 25%, satisfactory photochromic property can be obtained at 560° to 700° C. with Fe₂O₃ provided by 1.0%. With Fe₂O₃ provided by 2.0%, however, the photochromic property is rather deteriorated.

Researches were conducted concerning low temperature calcinating, using the urea process. Tests were conducted by using anatase/rutile=50/50 as material titanium oxide and varying the amount of Fe₂O₃.

TABLE 17

Urea process
(anatase/rutile = 50/50, specific surface area; 98 m²/g, Fe₂O₃: 0.7%)

| Calcinating temperature | 560 | 600 | 660 | 700 |
|---|---|---|---|---|
| ΔE after ultra-violet ray irradiation for 30 minutes | 4.58 | 4.76 | 4.74 | 6.46 |
| (A) | Δ | Δ | Δ | ○ |
| ΔE after leaving in dark place for 60 minutes | 1.39 | 1.62 | 2.60 | 4.58 |
| Restoration factor | 70% | 66% | 46% | 30% |
| ΔE after leaving in dark place for 120 minutes | 1.26 | 1.37 | 2.14 | 4.11 |
| Restoration factor | 73% | 72% | 55% | 37% |
| ΔE after leaving in dark place for 24 hours | 1.02 | 1.01 | 1.02 | 2.47 |
| (B) | ○ | ○ | ○ | ○ |
| Restoration factor | 78% | 79% | 79% | 62% |

TABLE 18

Urea process
(anatase/rutile = 50/50, specific surface area: 98 m²/g, Fe₂O₃: 1.5%)

| Calcinating temperature | 560 | 600 | 660 | 700 |
|---|---|---|---|---|
| ΔE after ultra-violet ray irradiation for 30 minutes | 5.36 | 5.75 | 6.10 | 8.06 |
| (A) | ○ | ○ | ○ | ○ |
| ΔE after leaving in dark place for 60 minutes | 1.87 | 2.65 | 3.62 | 6.05 |
| Restoration factor | 66% | 54% | 41% | 25% |
| ΔE after leaving in dark place for 120 minutes | 1.48 | 2.21 | 3.15 | 5.48 |
| Restoration factor | 73% | 62% | 49% | 33% |
| ΔE after leaving in dark place for 24 hours | 0.94 | 1.17 | 1.78 | 3.56 |
| (B) | ○ | ○ | ○ | Δ |
| Restoration factor | 83% | 80% | 71% | 42% |

TABLE 19

Urea process
(anatase/rutile = 50/50 specific surface area: 98 m²/g, Fe₂O₃: 3.0%)

| Calcinating temperature | 560 | 600 | 660 | 700 |
|---|---|---|---|---|
| ΔE after ultra-violet ray irradiation for 30 minutes | 4.44 | 4.45 | 5.62 | 6.61 |
| (A) | Δ | Δ | ○ | ○ |
| ΔE after leaving in dark place for 60 minutes | 1.87 | 1.78 | 3.52 | 5.15 |
| Restoration factor | 58% | 60% | 88% | 23% |
| ΔE after leaving in dark place for 120 minutes | 1.54 | 1.41 | 3.28 | 4.68 |
| Restoration factor | 66% | 69% | 42% | 30% |
| ΔE after leaving in dark place for 24 hours | 0.89 | 0.66 | 2.09 | 3.50 |
| (B) | ○ | ○ | ○ | Δ |
| Restoration factor | 80% | 86% | 63% | 48% |

As is seen from the above, where anatase/rutile=50/50 is used as material titanium oxide for manufacture with the urea process, the color change degree is rather small if the calcinating is effected in a low temperature range. However, by slightly increasing the content of iron as active agent (i.e. Fe₂O₃: 1.5%) satisfactory photochromic property can be obtained at 560° to 700° C.

As shown above, it was made clear that so far as fine particle titanium oxide is concerned sufficient photochromic property could be obtained at a calcinating temperature lower than the common sense calcinating temperature in the prior art.

The inventors further tried calcinating at 400° to 500° C.

TABLE 20

Urea process
(anatase type, specific surface area: 100 m²/g, 0.7% Fe₂O₃)

| Calcinating temperature | 400 | 500 |
|---|---|---|
| ΔE after ultra-violet ray irradiation for 30 minutes | 7.14 | 8.94 |
| (A) | ○ | ○ |
| ΔE after leaving in dark place for 60 minutes | 3.49 | 3.70 |
| Restoration factor | 52% | 59% |
| ΔE after leaving in dark place for 120 minutes | 3.01 | 2.74 |
| Restoration factor | 58% | 70% |
| ΔE after leaving in dark place for 24 hours | 2.37 | 1.54 |
| (B) | ○ | ○ |
| Restoration factor | 67% | 83% |

TABLE 21

Urea process
(anatase type, specific surface area: 100 m²/g, 1.5% Fe₂O₃)

| | | |
|---|---|---|
| Calcinating temperature | 400 | 500 |
| ΔE after ultra-violet ray irradiation for 30 minutes | 5.32 | 6.25 |
| (A) | ○ | ○ |
| ΔE after leaving in dark place for 60 minutes | 1.82 | 2.46 |
| Restoration factor | 66% | 61% |
| ΔE after leaving in dark place for 120 minutes | 1.53 | 2.06 |
| Restoration factor | 72% | 68% |
| ΔE after leaving in dark place for 24 hours | 0.83 | 1.21 |
| (B) | ○ | ○ |
| Restoration factor | 85% | 81% |

TABLE 22

Urea process
(anatase type, specific surface area: 100 m²/g, 3.0% Fe₂O₃)

| | | |
|---|---|---|
| Calcinating temperature | 400 | 500 |
| ΔE after ultra-violet ray irradiation for 30 minutes | 6.25 | 6.76 |
| (A) | ○ | ○ |
| ΔE after leaving in dark place for 60 minutes | 3.43 | 4.10 |
| Restoration factor | 45% | 39% |
| ΔE after leaving in dark place for 120 minutes | 2.98 | 3.71 |
| Restoration factor | 58% | 45% |
| ΔE after leaving in dark place for 24 hours | 1.75 | 2.40 |
| (B) | ○ | ○ |
| Restoration factor | 72% | 64% |

As is seen from Tables 20 to 22, so far as fine particle titanium oxide is concerned, sufficient photochromic property can be imparted even at a calcinating temperature of about 400° C.

Amount of active agent added and photochromic pro

Researches were conducted concerning the amount of iron oxide added as active agent and photochromic property.

When the amount of the active agent added is increased, coloring is sometimes produced. In this case, the sample is no longer suited for the observation of the photochromic property.

Accordingly, researches and investigations were conducted about the photochromic property in case when the amount of the active agent added is held low.

Test example 1 Synthesis from titanyl sulfate-iron (1)

800 ml of 2M TiOSO₄ aqueous solution was prepared, and FeCl₂ aqueous solution such as to provide three different levels of % by weight of Fe₂O₃ with respect to TiO₂, i.e., 0.7, 1.5 and 3.0% were added to the TiOSO₄ aqueous solution. Subsequently, the resultant system was heated for 4 hours and then cooled down to room temperature, followed by filtering and washing with writer. Then, the pH was adjusted to 8 with a NaOH aqueous solution, and the system was then washed with water again and dried.

This fine particle titanium oxide was calcinated at 500° to 800° C.

First, anatase type was investigated by varying the amount of Fe₂O₃.

TABLE 23

Urea process
(anatase, specific surface area: 48 m²/g, 0.7% Fe₂O₃)

| | | | | |
|---|---|---|---|---|
| Calcinating temperature | 580 | 600 | 660 | 700 |
| ΔE after ultra-violet ray irradiation for 30 minutes | 8.15 | 7.74 | 6.85 | 9.57 |
| (A) | ○ | ○ | ○ | ○ |
| ΔE after leaving in dark place for 60 minutes | 3.31 | 3.91 | 4.21 | 7.30 |
| Restoration factor | 59% | 49% | 39% | 24% |
| ΔE after leaving in dark place for 120 minutes | 2.44 | 3.31 | 3.79 | 6.80 |
| Restoration factor | 70% | 57% | 45% | 29% |
| ΔE after leaving in dark place for 24 hours | 1.26 | 1.71 | 1.94 | 4.23 |
| (B) | ○ | ○ | ○ | X |
| Restoration factor | 85% | 78% | 72% | 56% |

TABLE 24

Urea process
(anatase, specific surface area: 100 m²/g, 1.5% Fe₂O₃)

| | | | | |
|---|---|---|---|---|
| Calcinating temperature | 560 | 600 | 660 | 700 |
| ΔE after ultra-violet lay irradiation for 30 minutes | 5.40 | 5.33 | 6.98 | 6.15 |
| (A) | ○ | ○ | ○ | ○ |
| ΔE after leaving in dark place for 60 minutes | 2.16 | 2.39 | 3.22 | 3.62 |
| Restoration factor | 60% | 55% | 54% | 41% |
| ΔE after leaving in dark place for 120 minutes | 1.86 | 2.33 | 2.74 | 2.94 |
| Restoration factor | 66% | 56% | 61% | 52% |
| ΔE after leaving in dark place for 24 hours | 0.87 | 0.93 | 1.15 | 2.15 |
| (B) | ○ | ○ | ○ | ○ |
| Restoration factor | 84% | 83% | 84% | 65% |

TABLE 25

Urea process
(anatase, specific surface area: 100 m²/g, 3.0% Fe₂O₃)

| | | | | |
|---|---|---|---|---|
| Calcinating temperature | 560 | 600 | 660 | 700 |
| ΔE after ultra-violet ray irradiation for 30 minutes | 4.82 | 5.29 | 5.34 | 5.83 |
| (A) | △ | ○ | ○ | ○ |
| ΔE after leaving in dark place for 60 minutes | 2.77 | 2.69 | 3.49 | 4.44 |
| Restoration factor | 43% | 49% | 35% | 24% |
| ΔE after leaving in dark place for 120 minutes | 2.50 | 2.42 | 3.23 | 4.30 |
| Restoration factor | 48% | 54% | 40% | 26% |
| ΔE after leaving in dark place for 24 hours | 1.16 | 1.48 | 1.99 | 2.71 |
| (B) | ○ | ○ | ○ | ○ |
| Restoration factor | 76% | 72% | 63% | 54% |

It will be seen that when anatase type titanium oxide is used, excellent photochromic property can be obtained with any amount of Fe₂O₃.

Accordingly, researches were made on the status of the photochromic property exhibition using small quantity of active agent.

800 ml of 2M TiOSO₄ aqueous solution was prepared and FeCl₃ aqueous solutions such as to provide five different levels of % by weight of Fe₂O₃ with respect to TiO₂, i.e., 0.01, 0.05, 0.125, 0.25 and 0.5% were added in the TiOSO₄ aqueous solution. Subsequently, the resultant system was heated or 4 hours and then cooled down to room temperature followed by filtering and washing with water. Then, the pH was adjusted to 8 with a NaOH aqueous solution, and the system was then washed again with water and dried.

TABLE 26

| 600° C. | | | | | |
|---|---|---|---|---|---|
| $Fe_2O_3$ | 0.01 | 0.05 | 0.125 | 0.25 | 0.5 |
| ΔE ultraviolet irradiation for 30 minutes | 2.17 | 4.68 | 8.45 | 10.16 | 10.20 |
| (A) | X | Δ | ○ | ○ | ○ |
| ΔE after leaving in dark place for 60 minutes | 0.65 | 1.69 | 5.25 | 6.75 | 6.93 |
| ΔE after leaving in dark place for 180 minutes | 1.01 | 0.94 | 3.70 | 4.71 | 5.10 |
| ΔE after leaving in dark place for 24 hours | 0.98 | 0.88 | 0.27 | 2.10 | 1.70 |
| (B) | ○ | ○ | ○ | ○ | ○ |
| Restoration factor | 55% | 81% | 77% | 79% | 83% |

TABLE 27

| 700° C. | | | | | |
|---|---|---|---|---|---|
| $Fe_2O_3$ | 0.01 | 0.05 | 0.125 | 0.25 | 0.5 |
| ΔE after ultra-violet ray irradiation for 30 minutes | 1.92 | 7.89 | 7.11 | 8.31 | 8.09 |
| (A) | X | ○ | ○ | ○ | ○ |
| ΔE after leaving in dark place for 60 minutes | 0.63 | 5.08 | 4.38 | 6.54 | 6.58 |
| ΔE after leaving in dark place for 180 minutes | 0.93 | 3.89 | 3.49 | 5.79 | 5.64 |
| ΔE after leaving in dark place for 24 hours | 0.89 | 2.32 | 1.56 | 3.74 | 3.23 |
| (B) | ○ | ○ | ○ | ○ | ○ |
| Restoration factor | 54% | 71% | 78% | 55% | 60% |

TABLE 28

| 800° C. | | | | | |
|---|---|---|---|---|---|
| $Fe_2O_3$ | 0.01 | 0.05 | 0.125 | 0.25 | 0.5 |
| ΔE after ultra-violet ray irradiation for 30 minutes | 1.54 | 4.44 | 6.11 | 5.25 | 6.34 |
| (A) | X | Δ | ○ | ○ | ○ |
| ΔE after leaving in dark place for 60 minutes | 1.05 | 2.66 | 3.71 | 3.54 | 4.43 |
| ΔE after leaving in dark place for 180 minutes | 1.18 | 2.19 | 2.89 | 3.04 | 3.78 |
| ΔE after leaving in dark place for 24 hours | 1.00 | 1.24 | 1.49 | 1.42 | 1.52 |
| (B) | ○ | ○ | ○ | ○ | ○ |
| Restoration factor | 35% | 72% | 76% | 73% | 76% |

As the result of the above test, it was made clear that when Using anatase type titanium oxide, it is suitable to add an active agent by 0.25 to 0.5% by weight in terms of $Fe_2O_3$.

Low temperature calcinating tests were further conducted on these particularly satisfactorily photochromic samples.

TABLE 29

| 500° C. | | |
|---|---|---|
| $Fe_2O_3$ | 0.25 | 0.5 |
| ΔE after ultra-violet ray irradiation for 30 minutes | 13.39 | 17.88 |
| (A) | ○ | ○ |
| ΔE after leaving in dark place for 60 minutes | 7.64 | 13.69 |
| ΔE after leaving in dark place for | 3.02 | 11.44 |

TABLE 29-continued

| 500° C. | | |
|---|---|---|
| 180 minutes | | |
| ΔE after leaving in dark place for 24 hours | 0.44 | 6.11 |
| (B) | ○ | X |
| Restoration factor | 97% | 66% |

TABLE 30

| 550° C. | | |
|---|---|---|
| $Fe_2O_3$ | 0.25 | 0.5 |
| ΔE after ultra-violet ray irradiation for 30 minutes | 7.39 | 13.58 |
| (A) | ○ | ○ |
| ΔE after leaving in dark place for 60 minutes | 4.42 | 10.15 |
| ΔE after leaving in dark place for 180 minutes | 1.72 | 7.96 |
| ΔE after leaving in dark place for 24 hours | 0.59 | 3.71 |
| (B) | ○ | Δ |
| Restoration factor | 92% | 73% |

It will be understood that very satisfactory color change degree and restoration factor can be obtained by adding 0.25% of $Fe_2O_3$ as active agent and carrying out calcinating 500° to 550° C.

While the specific surface area of the material titanium oxide is 181 m²/g, after calcinating at 600° C. the specific surface area is 45.9 m²/g. Thus, the specific surface area is maintained satisfactorily.

Photochromic titanium oxide and ultra-violet ray shield effect

From the above various experiments, it is made clear that for obtaining excellent photochromic property by calcinating at a comparatively low temperature below 700° C. it is suitable to incorporate 50% or more of anatase type titanium oxide and incorporate iron, if used as active agent, by about 0.25% by weight in terms of $Fe_2O_3$.

Meanwhile, the specific surface area and calcinating temperature of titanium oxide are very closely related to each other as noted earlier.

Accordingly, researches were conducted about the correlation between the calcinating temperature and specific surface area.

Figure 4:
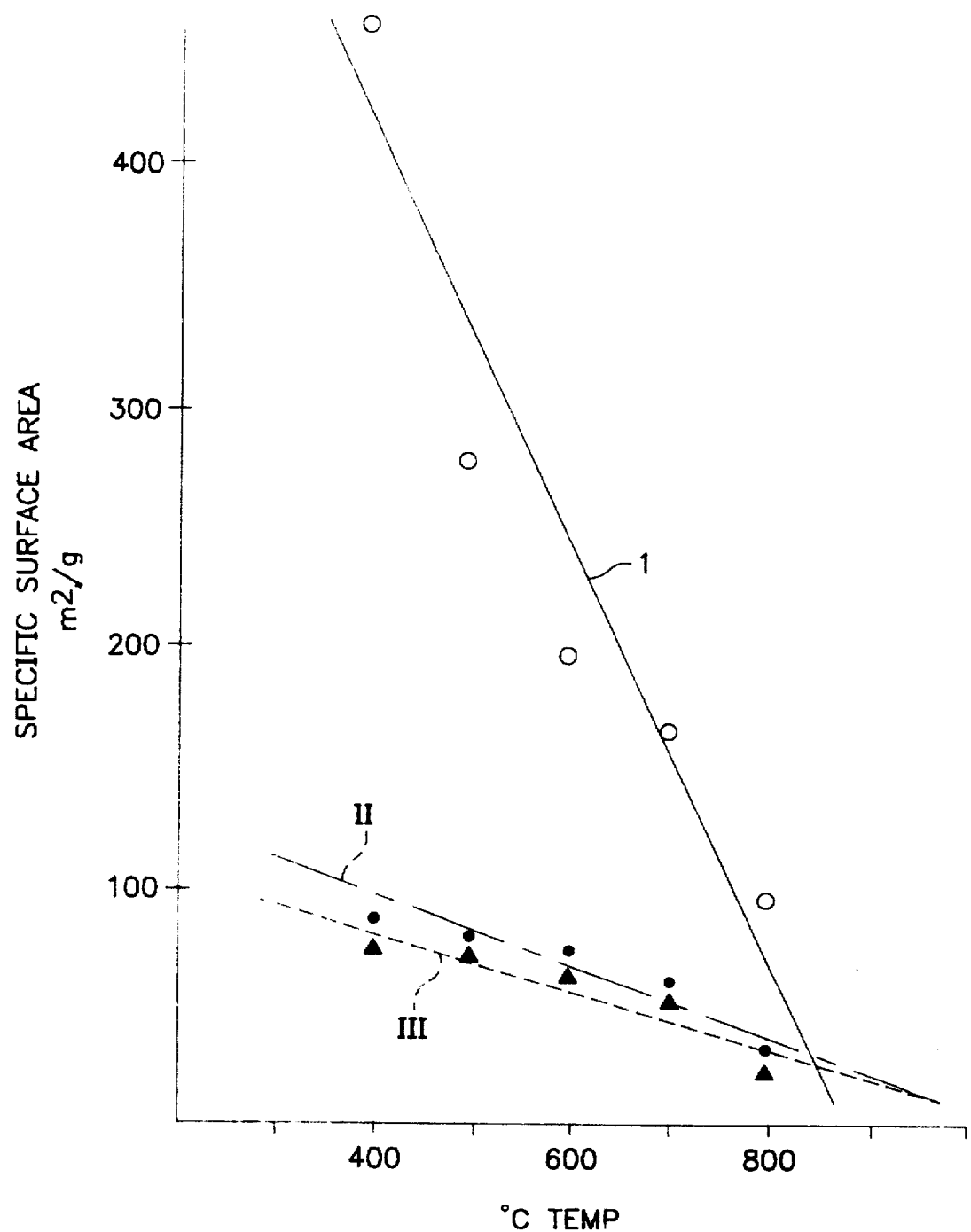
FIG. 4 is a graph showing the relation between the specific surface area and calcinating temperature of titanium oxide samples having different specific surface areas.

FIG. 4 shows the relation between the specific surface area and the calcinating temperature.

In the Figure, all the plots have downward slopes toward the right and substantially straight. They can be given as S=bT+a with S being the specific surface area of powder after calcinating, T being the calcinating temperature, and a and b constants The plot line I the relation between the surface are $S_1$ and temperature T in case amorphous titanium oxide of 700 m²/g, obtained by the liquid phase process from Ti(O-iso-Pr)$_4$, was calcinated at various temperatures.

As a result of this regressive analysis, the following relation could be obtained.

$S_1 = -0.876T + 768$.

The phantom line plot II shows the relation between the specific surface area $S_2$ and temperature T in case when anatase type titanium oxide of 100 m²/g, obtained by the liquid phase process from Ti(O-iso-Pr)$_4$, was calcinated at various temperatures.

As a result of this regressive analysis, the following relation could be obtained.

$$S_1 = -0.125T + 140$$

The dashed line plot III shows the relation between the surface area $S_1$ and temperature T in case when amorphous titanium oxide of 100 m²/g, obtained by the gaseous phase process from TiCl$_4$, was calcinated at various temperatures.

As a result of this regressive analysis, the following relation could be obtained.

$$S_1 = -0.123T + 129$$

Further, although not shown, in case when titanium oxide with a specific surface area of 55 m²/g and with amorphous/ rutile=75/25, obtained by the gaseous phase process from TiCl$_4$, regressive analysis yielded the following relation.

$$S_1 = -0.10T + 90$$

Thus, it will be understood that The constant a assumes a value of the sum of the specific surface area $S_0$ before the calcinating and about 30 to 70, while the constant b is reduced substantially in, inverse proportion to the specific surface area before the calcinating.

In either case, in either plot, when the calcinating temperature exceeds 700° C., the specific surface area is undesirably extremely reduced. Further, regarding file particle titanium oxide, sufficient photochromic property can be obtained at a temperature not higher than 700° C., particularly not higher than 600° C., as noted above. Thus, a suitable calcinating temperature range is 400° C.$\leq T \leq$600° C.

When the material titanium oxide used has a specific surface area of 100 m²/g or above, sufficient specific surface area and photochromic property can be obtained in a range of 700° C.

When the material titanium oxide used has a specific surface area of 100 m²/g, it is possible to use b=-0.10 and a=$S_0$+35 ($S_0$ being the specific surface area of the powder after the calcinating) for satisfactorily calculating the specific surface area of the powder after the calcinating.

Thus, with titanium oxide having a specific surface area of 100 m²/g or below used as material, if the minimum specific surface area of the powder after the calcinating is 25 m²/g, the upper limit of the calcinating temperature can be calculated from $$25 = -0.10T + (S_0 + 35)$$

$$T = (S_0 + 10)/0.10$$

Accordingly, material titanium oxide containing 50% or more of anatase type titanium oxide was actually calcinated at 700° C. or below, and the ultra-violet ray shield effect of the calcinated material was investigated.

First, the specific surface area of each photochromic titanium oxide was investigated.

TABLE 31

| Material titanium oxide | Specific surface area | Treatment process | Fe$_2$O$_3$ | calcinating temperature | Specific surface area after calcinating |
|---|---|---|---|---|---|
| Anatase | 98 m²/g | Neutralization | 0.7% | 700° C. | 39.2 m²/g |
| Same | Same | Same | same | 660 | 52.2 |
| Same | Same | Same | same | 600 | 67.0 |
| Same | Same | Urea | same | 700 | 40.0 |
| Same | Same | Same | same | 660 | 47.0 |
| Same | Same | Same | same | 600 | 68.5 |

It will be understood that each sample- of calcinated titanium oxide has a specific surface area of 40 m²/g or above, that is, it maintains particle sizes 40 to 70 m²/g in terms of the specific surface area range, which is particularly suitable with respect to the ultraviolet scattering.

Specific researches were conducted concerning the ultraviolet scattering effects.

Samples were prepared as follows.

(1) Neutralization process (photochromic ultraviolet ray shield powder samples 1 to 3)

100 g of titanium oxide (anatase type, specific surface area: 98 m²/g) was dispersed in 2,000 ml of deionized water. Then, 10.5 g of iron chloride FeCl$_3$ was added, and the system was stirred. Then, about 10 g of sodium hydroxide was added for neutralization to pH 8 (shield powder sample 1), pH 9 (shield powder sample 2) and pH 10 (shield powder sample 3), followed by reaction at 80° to 90° C. for 2 hours. Then, each system was filtered, and the residue was washed with water and dried. The dry residue was then calcinated at 600° C. and disintegrated. As comparative example, calcinating was effected at 800° C.

Each test sample was diluted to 5% in a blend solution composed of 95% of castor oil and 5% of "Cosmol⁷" (Sorbitan sesqui oleate) and then coated using an applicator to a thickness of 10 μm for measurement.

Figure 5:
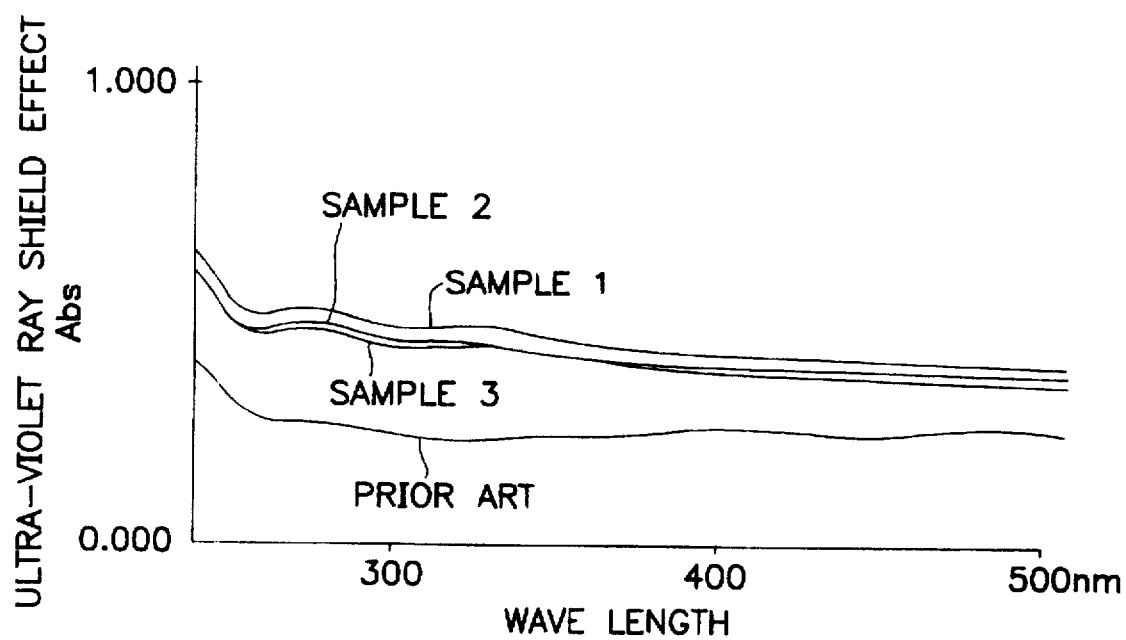
FIGS. 5 to 8 are graphs showing ultra-violet ray shield effects of photochromic ultra-violet ray shield powder according to the invention.

FIG. 5 shows the ultra-violet ray shield effect.

As is clear from the Figure, all the shield powder samples 1 to 3 show excellent shield effect with respect to ultra-violet rays of 300 to 400 nm. There was a trend for the slightly higher effect obtainable with the lower pH.

(2) Urea process (photochromic ultra-violet ray shield powder samples 4 to 6)

40 g of titanium oxide (anatase type, 98 m²/g) was dispersed in 800 ml of deionized water, then 0.41 g of ion chloride FeCl$_3$ was added, and the system was then stirred. Then, 5 ml of 5% sodium hydroxides aqueous solution was added for neutralization. Then, 1.29 g of area was added and the system was reacted at 90° to 98° C. for 3 hours. Then, the samples were filtered, and the residues were washed with water and dried. Then, calcinating was done at 400° C. (sample 4). 600° C. (sample 5) and 700° C. (sample 6), and each sample was then disintegrated. The measurement was done in the same way as with the above samples 1 to 3.

Figure 6:
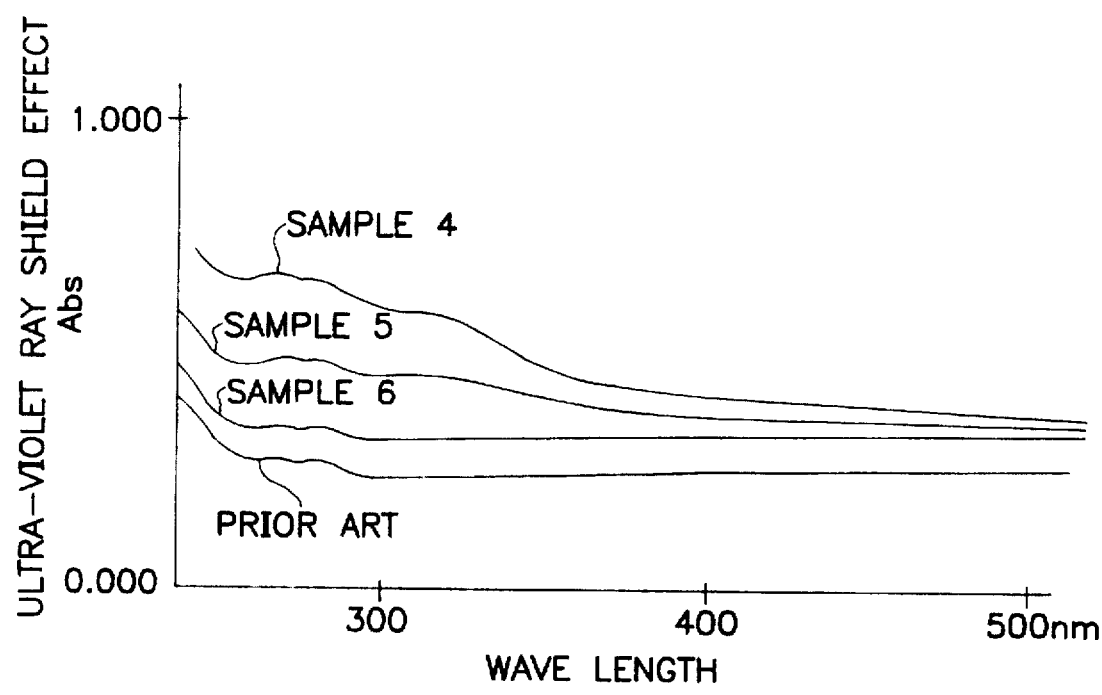

FIG. 6 shows the ultra-violet ray shield effect.

As is clear from the Figure the more excellent ultra-violet ray shield effect is obtainable with the lower calcinating temperature.

(3) Urea process (photochromic ultra-violet ray shield powder samples 7 and 8)

Titanium oxide (anatase type, 100 m$_2$/g) was prepared such that Fe$_2$ was 0.7%, and then calcinated at 560° C. (sample 7) and 600° C. (sample 8).

Figure 7:
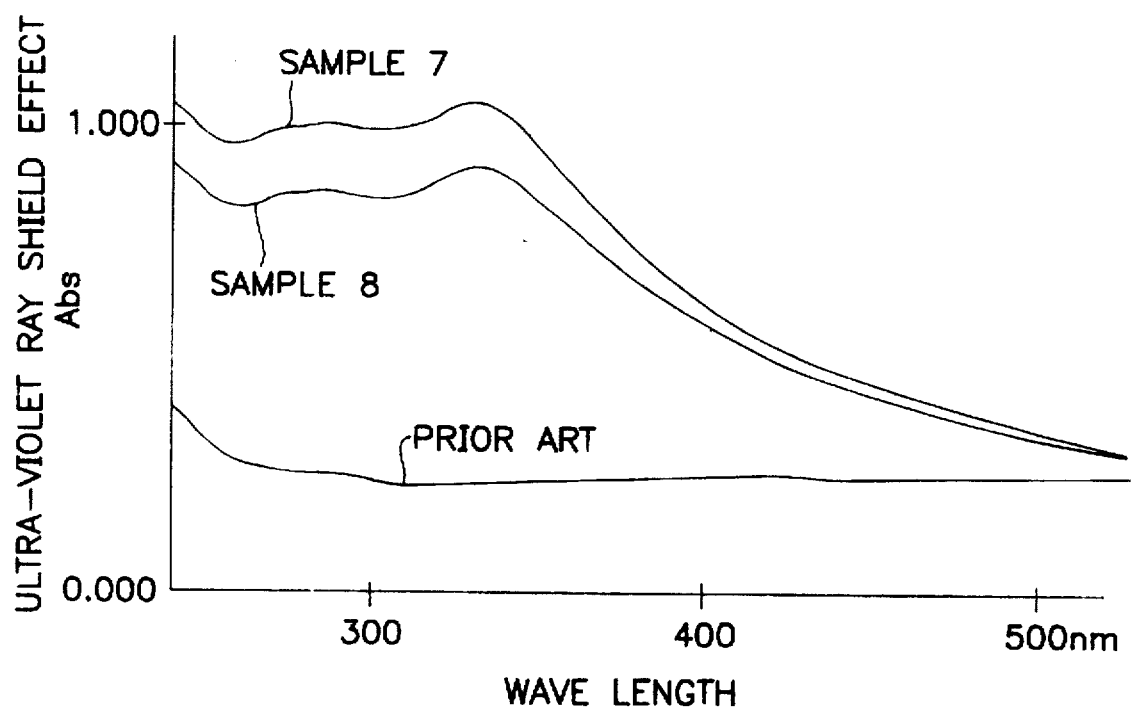

FIG. 7 shows the ultra-violet ray shield effect of the photochromic ultra-violet ray shield powder samples.

It will be seen that in this case very excellent ultra-violet ray shield effect can be obtained compared to the cases of FIGS. 5 and 6.

Now, examples of the manufacture of the photochromic ultra-violet ray shield powder according to the invention will be described.

Example 1

While stirring a solution obtained by diluting 100 parts of titanium tetra-iso-propoxide with 500 parts of iso-propanol, a solution obtained by diluting 50 parts of water with 500 parts of iso-propanol, was added for hydrolysis.

To this suspension was added a solution obtained by dissolving 5 parts of ferrous chloride in ethanol, and the resultant system was subjected to a surface treatment with its pH adjusted to about 10 using sodium hydroxide. This suspension was condensed using suction filter means, and then dried at 120 to obtain 40 parts of stable fine particle powder with a specific surface area of about 700 $m^2/g$.

This fine particle powder was calcinated at the following temperatures. As a result, the following specific surface areas and photochromic properties could be obtained.

TABLE 32

| Calcinating temperature | 400 | 500 | 600 | 700 |
|---|---|---|---|---|
| Specific surface area | 475.7 | 278.6 | 197.3 | 165.2 |
| ΔE after ultra-violet ray irradiation for 30 minutes | 6.39 | 5.94 | 5.02 | 3.42 |
| (A) | ○ | ○ | ○ | X |
| ΔE after leaving in dark place for 60 minutes | 2.56 | 2.59 | 3.86 | 2.56 |
| ΔE after leaving in dark place for 120 minutes | 2.27 | 2.29 | 2.39 | 2.35 |
| ΔE after leaving in dark place for 24 hours | 1.16 | 1.20 | 1.70 | 1.21 |
| (B) | ○ | ○ | ○ | ○ |
| Restoration factor | 81% | 79% | 66% | 64% |

Example 2

Anatase type titanium oxide with a specific surface area of 100 $m^2/g$ was produced from $TiOSO_4$ by the liquid phase process, and photochromic ultra-violet ray shield powder was produced by using 1.5% of $Fe_2O_3$ as an active agent.

The following specific surface areas and photochromic properties could be obtained.

TABLE 33

| Calcinating temperature | 450 | 500 | 550 | 600 | 700 |
|---|---|---|---|---|---|
| Specific surface area | 67.3 | 61.6 | 55.9 | 58.4 | 37.6 |
| ΔE after ultra-violet ray irradiation for 30 minutes | 6.39 | 5.62 | 5.49 | 5.99 | 7.77 |
| (A) | ○ | ○ | ○ | ○ | ○ |
| ΔE after leaving in dark place for 60 minutes | 3.52 | 3.25 | 3.26 | 3.60 | 5.61 |
| ΔE after leaving in dark place for 120 minutes | 3.08 | 2.95 | 3.01 | 3.25 | 5.18 |
| ΔE after leaving in dark place for 24 hours | 1.88 | 1.74 | 2.12 | 1.98 | 3.21 |
| (B) | ○ | ○ | ○ | ○ | Δ |
| Restoration factor | 71% | 70% | 62% | 67% | 59% |

Figure 8:
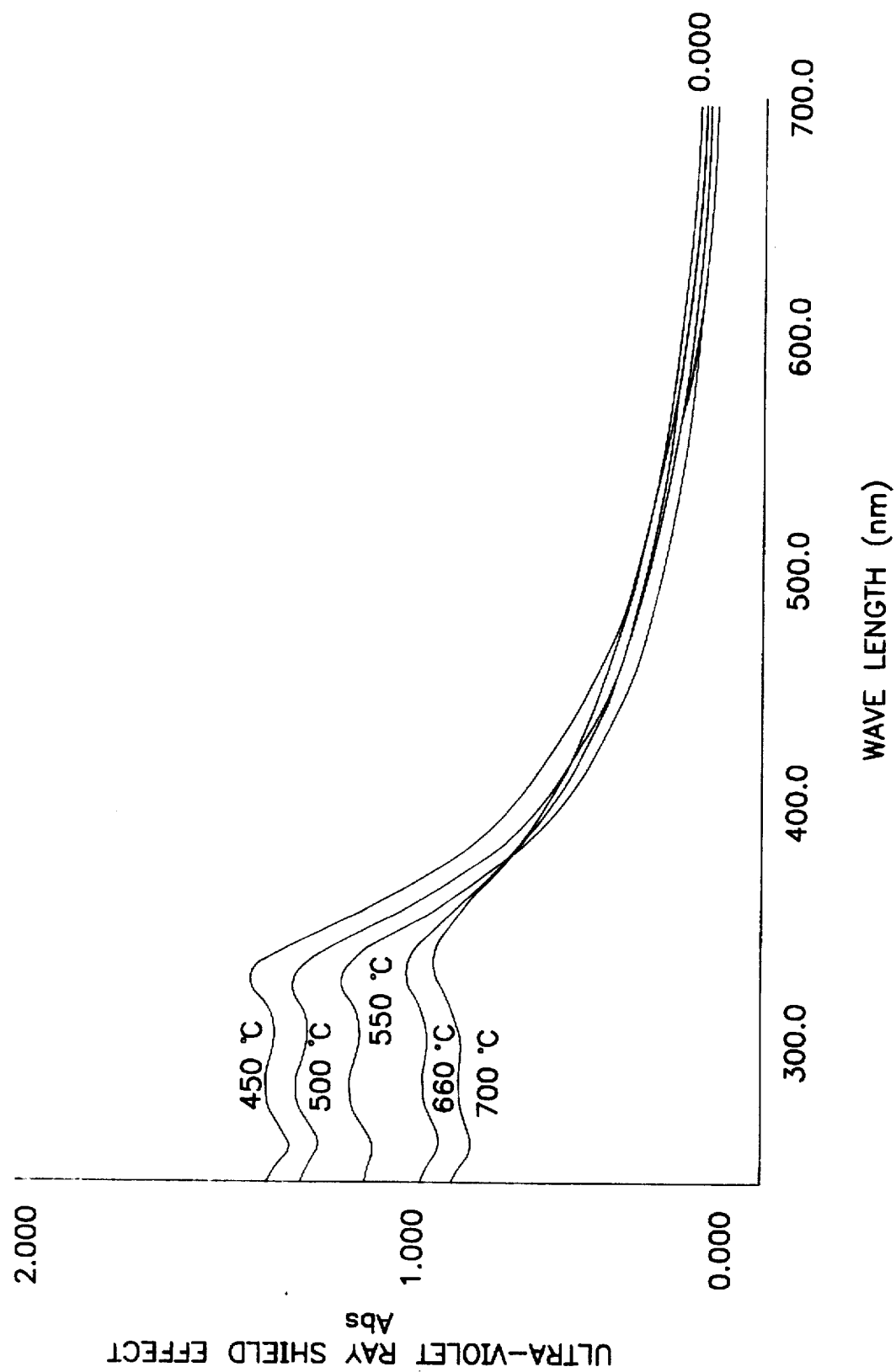

FIG. 8 shows specific ultra-violet ray shield effects.

In the Figure, the relation between the ultra-violet ray shield degree and the wavelength is shown in cases of calcinating temperatures of 450°, 500°, 550°, 660° and 700° C. It will seen from the Figure that while all the samples have excellent ultra-violet ray shield effects, the more satisfactory effects can be obtained the lower the calcinating temperature.

As for the difference, in the effect between the urea process and the neutralization processes, the effect was slightly better with the neutralization process, but the difference was not so much.

Example 3

In a first trough 100 parts of tetra-iso-propoxy titanium was heated at about 200° C., in a second trough 500 parts of water was heated at about 120° C., and air was introduced from each trough as carrier gas into an electric furnace at 300° C. for hydrolysis. Further, in a third trough 1.5 parts of zinc chloride was heated at about 800° C., and air was introduced from the trough into the same electric furnace for surface treatment. This powder was recovered using filter cloth to obtain 40 parts of material anatase type titanium oxide with a specific surface area of 100 $m^2/g$.

This powder was calcinated at 500° C. to obtain photochromic ultra-violet ray shield powder with A=5.05, B=2.01 and specific surface area of 79.0 $m^2/g$.

Examples of the composition using the photochromic ultra-violet ray shield powder as above according to the invention are given below. Each composition showed excellent photochromic property and ultra-violet ray shield effect.

Composition example 1 Pressed powder

| (1) Photochromic ultra-violet ray shield powder (sample 4) | 5.2% |
|---|---|
| (2) Talc | 90.0% |
| (3) Iron oxide | 2.5% |
| (4) Squalane | 2.0% |
| (5) Preservative agent | 0.2% |
| (6) Perfume | 0.1% |

(Method of manufacture)

The components (1) to (3) were mixed, and in this mixture the components (4) to (6) were thermally dissolved. The resultant system was disintegrated. The resultant particles were molded into the form or dishes, thus obtaining pressed powder.

Composition example 2 Powder foundation

| (1) Photochromic ultra-violet ray shield powder (sample 7) | 20.0% |
|---|---|
| (2) Talc | 10.0% |
| (3) Sericite | 47.9% |
| (4) Spherical nylon powder | 8.0% |
| (5) Red iron oxide | 0.5% |
| (6) Yellow iron oxide | 1.0% |
| (7) Black iron oxide | 0.1% |
| (8) Polydimethyl siloxane | 5.0% |
| (9) 2-ethylhexyl palmitate | 5.0% |
| (10) Sorbitan sesquioleate | 1.5% |
| (11) Preservative agent | 0.9% |
| (12) Perfume | 0.1% |

(Method of manufacture)

The components (1) to (9) were mixed using a Henshell Mixer mixer. To this mixture was added what was obtained by thermally dissolving and mixing the components (9) to (12). The resultant system was disintegrated using a Pulverizer (by Hosokawa Mikuron). The resulant particles were then molded into the form of a dish, thus obtaining a powder foundation.

Composition example 3 Dual purpose foundation

| (1) Photochromic ultra-violet ray shield powder (sample 1) | 5.0% |
|---|---|
| (2) Silicone-treated mica | 46.25% |
| (3) Silicone-treated talc | 25.0% |
| (4) Silicone-treated iron oxide | 4.5% |
| (5) Silicone-treated titanium oxide | 6.5% |

|  |  |
|---|---|
| (6) Trimethylolpropane triisostearate | 5.0% |
| (7) Squalane | 3.0% |
| (8) Bees was | 2.0% |
| (9) Sorbitan Trioleate | 1.0% |
| (10) Preservative agent | 0.5% |
| (11) Vitamin E | 0.05% |
| (12) Butylmethoxybenzoil methane | 1.0% |
| (13) Perfume | 0.2% |

(Method of manufacture)

The components (1) to (5) were mixed. To this mixture was added what was obtained by thermally dissolving the components (6) to (13). The system was then disintegrated. The obtained particles were molded to the shape of a disk to obtain a dual foundation.

Composition example 4 sun oil

|  |  |
|---|---|
| (1) Liquid paraffin | 69.75% |
| (2) Silicone oil | 20.0% |
| (3) Vitamin E | 0.05% |
| (4) Perfume | 0.2% |
| (5) Photochromic ultra-violet ray shield powder (sample 8) | 10.0% |

(Method of manufacture)

The components (1) to (4) were mixed, and then the component (5) was added and dispersed. Then, the system was degassed to obtain sun oil. The sun oil was darkened when exposed to sunlight, and also it has excellent ultra-violet ray shield effect.

Composition example 5 paint

|  |  |
|---|---|
| (1) Photochromic ultra-violet ray shield powder (sample 8) | 2.0% |
| (2) Acryloid B-66 | 22.0% |
| (3) Xylene | 56.0% |
| (4) Mineral spirit | 20.0% |

(Method of manufacture)

The components (1) to (5) were needed with a roll mill to obtain acrylic acid paint.

Composition example 6 Emulsified foundation

|  |  |
|---|---|
| (1) Photochromic ultra-violet ray shield powder (sample 7) | 1.0% |
| (2) Stearic acid | 1.5% |
| (3) Isostearic acid | 0.3% |
| (4) Isopropyl myristate | 4.0% |
| (5) Squalane | 12.0% |
| (6) POE stearylether | 1.5% |
| (7) Glyceryl monooleate | 0.5% |
| (8) Cetylalcohol | 0.5% |

|  |  |
|---|---|
| (9) Talc | 10.0% |
| (10) Iron oxide | 0.5% |
| (11) Preservative agent | 0.15% |
| (12) Triethanol amine | 0.8% |
| (13) Propylene glycol | 6.0% |
| (14) Montmorillonite | 0.5% |
| (15) Refined water | 60.55% |
| (16) Perfume | 0.2% |

(Method of manufacture)

The components (12) to (15) were mixed and heated to 70° C. Then the components (1) to (9) were mixed and disintegrated to be added to the first-mentioned mixture. Then, the oil components (2) to (8), (1) and (16) which were preliminary thermally dissolved and mixed at 70° C., were, gradually added. Then the system was subjected to emulsified dispersion. The resultant system was cooled down to room temperature to obtain an emusified foundation.

We claim:

1. A photochromic ultra-violet ray shield powder comprising particles of titanium oxide having a specific surface area of at least 25 m²/g and A≧5 and B≦3, wherein A represents a color difference ΔE between a color determined in test (1) and a color determined in a test (2), and B represents a color difference ΔE between a color determined in test (1) and a color determined in a test (3), and in the test:

(1) A sample is colorimetrically measured after it has been left a room temperature and in a dark place for about 10 hours, (2) A sample is immediately colorimetrically measured when it is darkened by irradiation with ultra-violet rays for 30 minutes in the same way as in test (1), and (3) An irradiated sample is similarly colorimetrically measured after leaving it at room temperature and in a dark place for 24 hours, and wherein said sample comprises an art paper having a dry nitrocellulose lacquer coating about 76 μm thick and comprising 25 wt. % of said shield powder, and wherein photochromic property measurements are made under an optical condition that a lamp of which $\lambda_{max}$ is 350 nm and power is 20 watts and a lamp of which $\lambda_{max}$ is 313 nm and power is 20 watts are secured a distance of 11 cm from each other, and distance adjustment of the sample is effected using an ultra-violet ray intensity measuring apparatus such that intensity of ultra-violet rays incident on the sample is 2 mW/cm².

* * * * *